United States Patent [19]

Dale et al.

[11] 4,274,838

[45] Jun. 23, 1981

[54] ANAEROBIC DIGESTER FOR ORGANIC WASTE

[75] Inventors: Eugene M. Dale, Montevallo, Ala.; Jerry A. Malstrom, Ludington, Mich.

[73] Assignee: Energy Harvest, Inc., Chicago, Ill.

[21] Appl. No.: 80,940

[22] Filed: Oct. 1, 1979

[51] Int. Cl.³ .................. C02F 11/04; C12M 1/04; C12P 5/02

[52] U.S. Cl. .................. 48/111; 48/197 A; 71/10; 210/608; 210/612; 210/629; 210/180; 435/313; 435/316; 435/801; 435/802; 435/167; 422/184; 422/230; 422/231

[58] Field of Search .............. 435/167, 290, 313, 315, 435/316, 287 (U.S. only), 291 (U.S. only), 801, 812; 48/197 A, 111; 71/10; 210/2, 12, 13, 14, 175, 180; 422/184, 200, 224, 230, 231, 232, 233

[56] References Cited

U.S. PATENT DOCUMENTS

| | | | |
|---|---|---|---|
| 1,314,955 | 9/1919 | Flicker | 210/12 |
| 1,690,682 | 11/1928 | Imhoff et al. | 435/167 X |
| 3,246,761 | 4/1966 | Bryan et al. | 48/197 A X |
| 3,981,803 | 9/1976 | Coulthard | 48/197 A X |
| 4,100,023 | 7/1978 | McDonald | 435/167 |
| 4,169,048 | 9/1979 | Albers, Sr. | 422/184 X |

*Primary Examiner*—Bradley Garris
*Attorney, Agent, or Firm*—McDougall, Hersh & Scott

[57] ABSTRACT

Organic wastes, such as animal manure, are fed into an elongated digester tank at one end thereof in slurry form. The slurry slowly moves to the other end of the tank for subsequent disposal. During the residence time in the tank decomposition of the waste occurs yielding methane gas and carbon dioxide. A cover over the digester collects the gas generated. A heat exchange arrangement causes transverse stirring of the slurry as it passes through the tank enhancing the decomposition process. Scum suppressors on the surface of the slurry prevent interference with the formation and release of the methane gas. The settling of solids is controlled by the use of gas jets disposed along the bottom of the tank.

8 Claims, 9 Drawing Figures

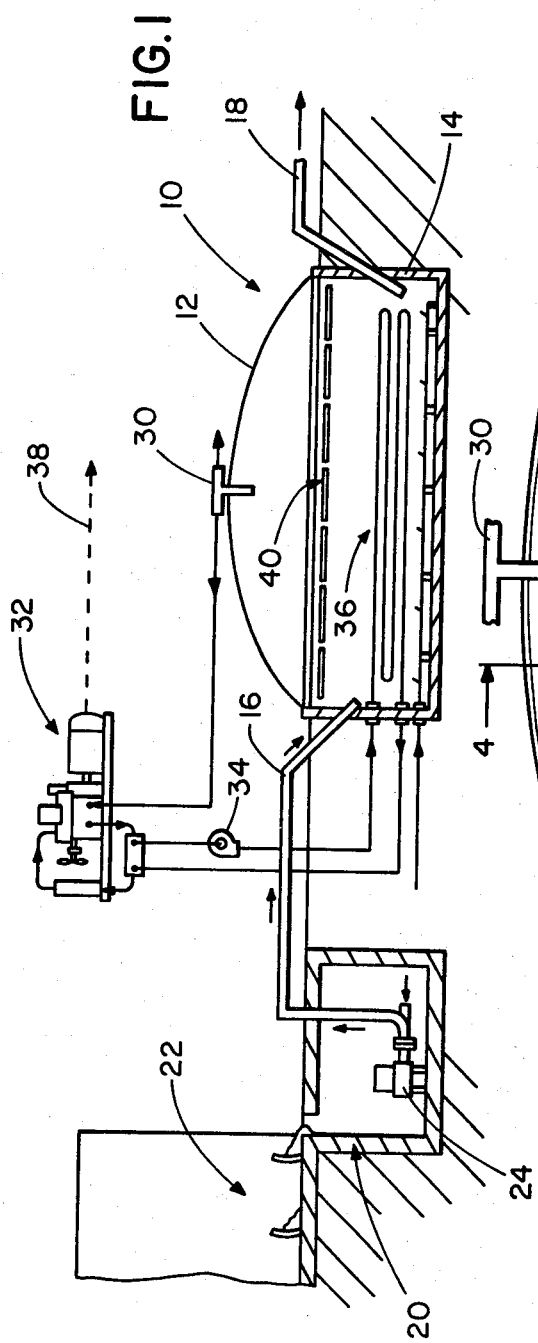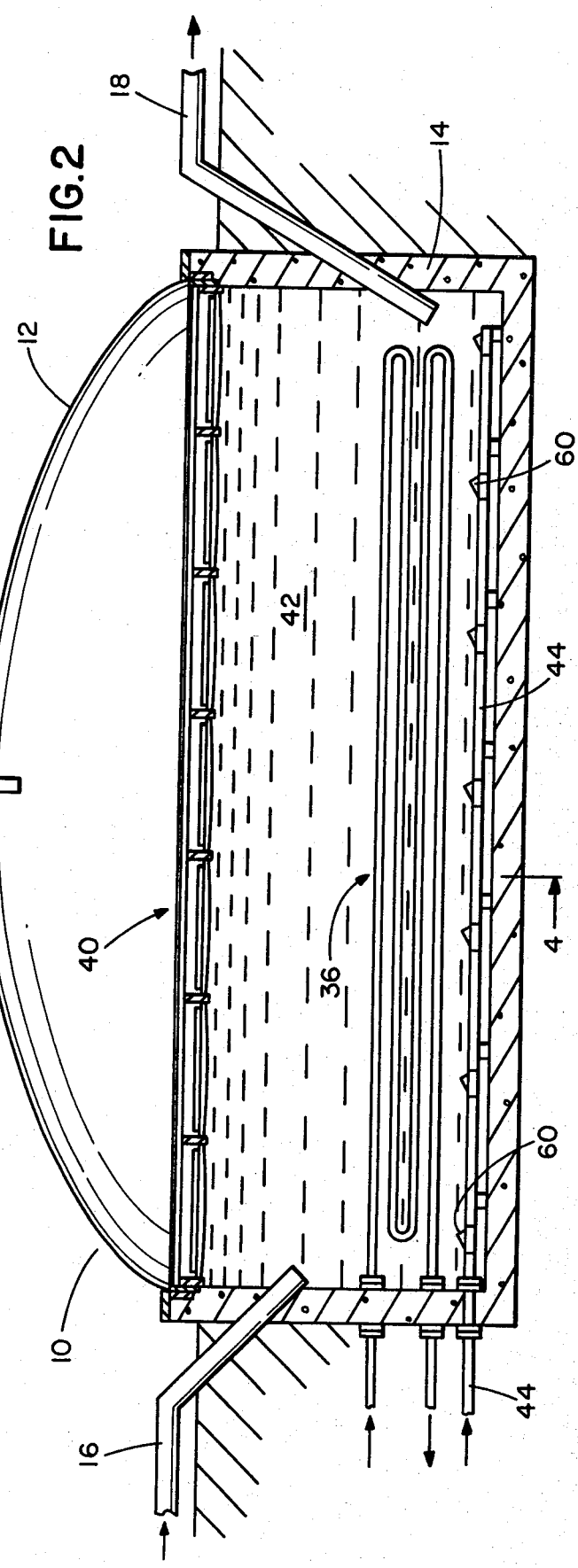

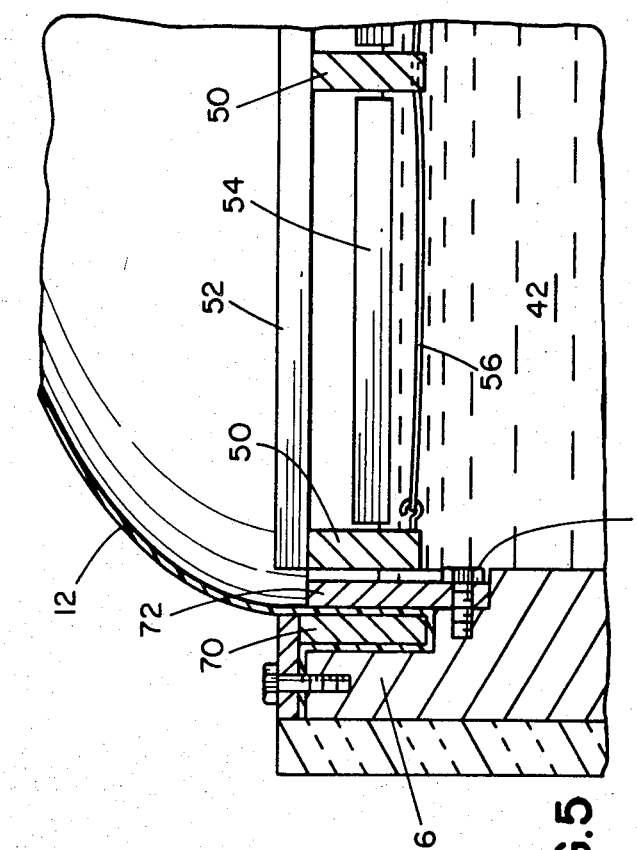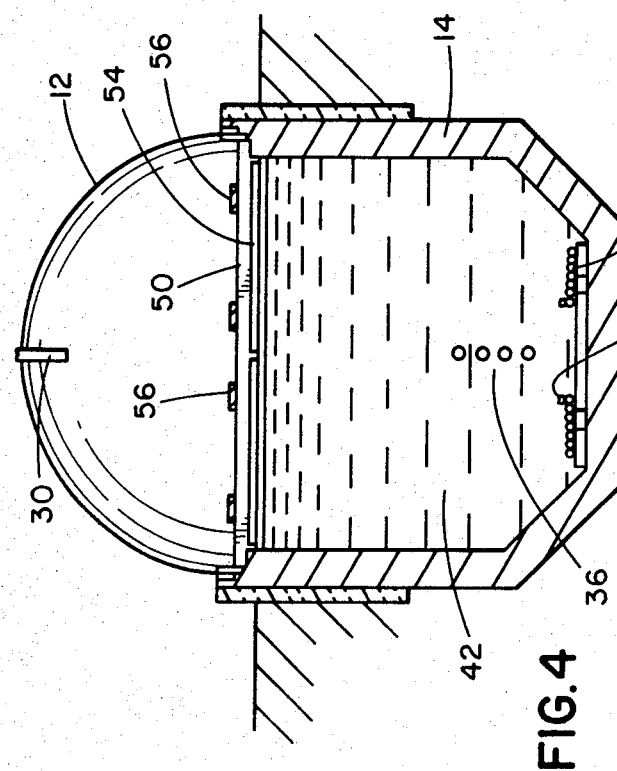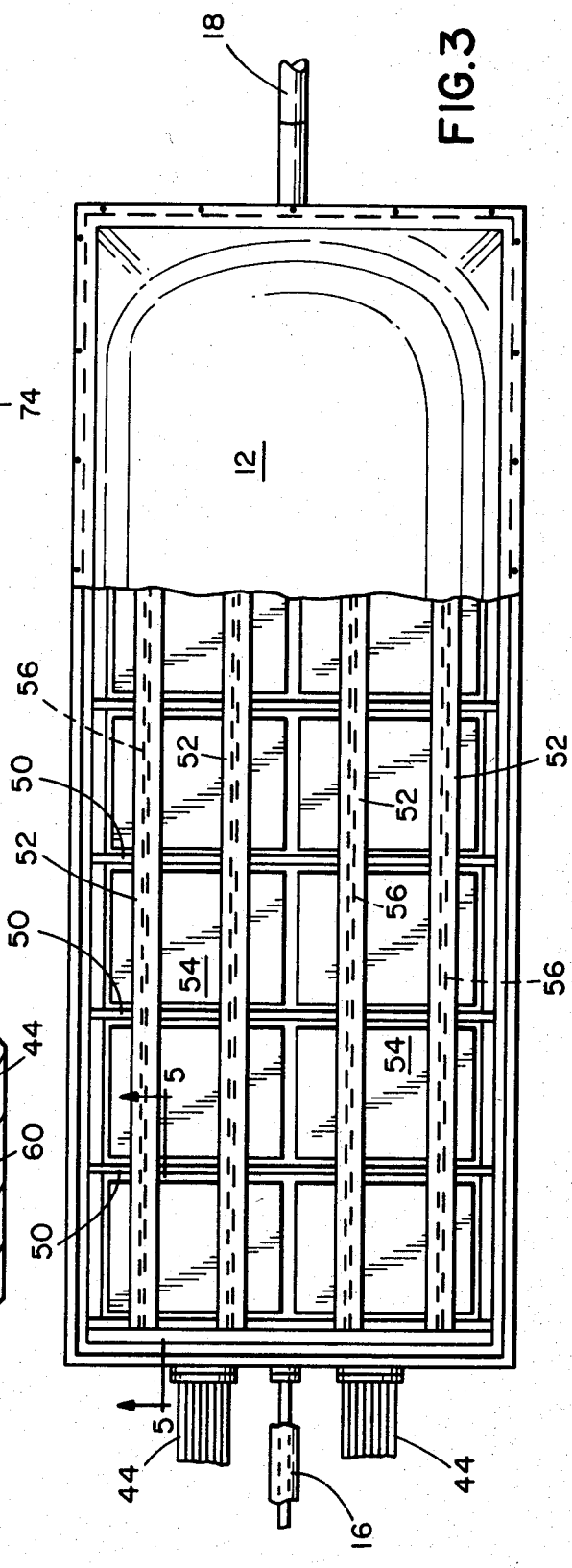

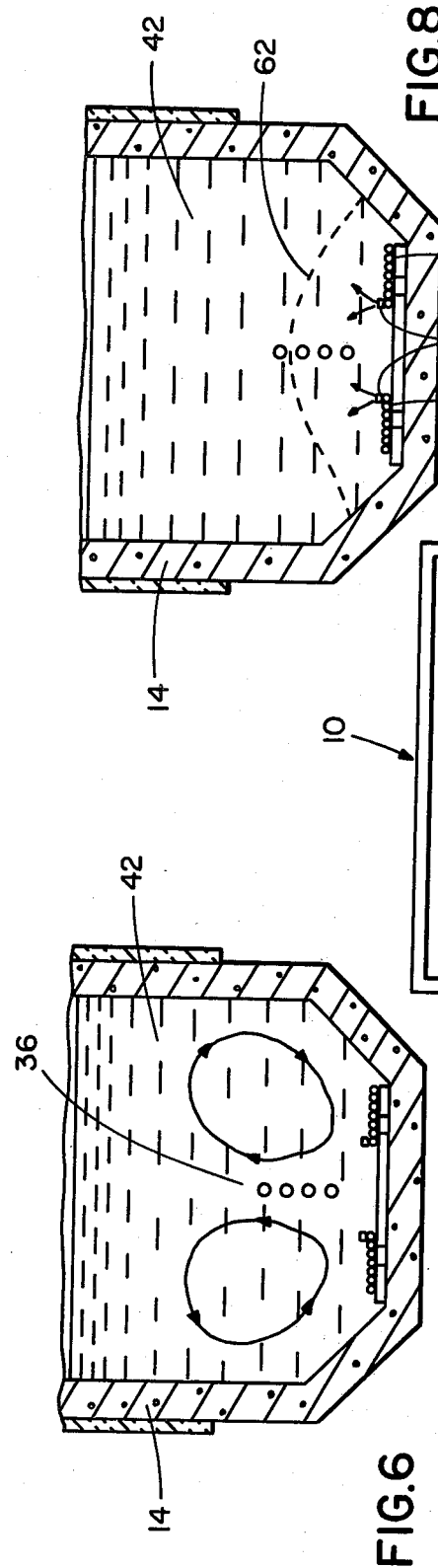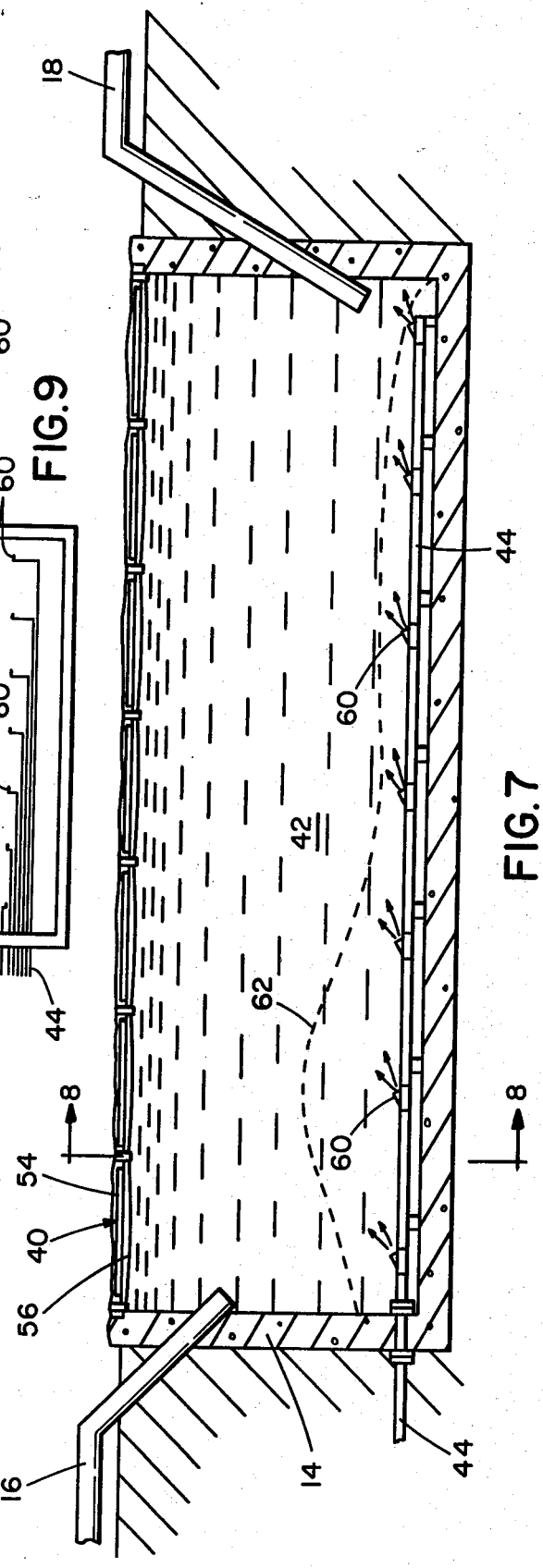

ANAEROBIC DIGESTER FOR ORGANIC WASTE

BACKGROUND OF THE INVENTION

This invention relates to the field of waste recovery. More particularly, it relates to the field of waste treatment wherein energy is recovered from organic wastes, such as animal manure, sludges or food processing wastes. Such wastes contain an enormous energy value if converted to useable form. It has been suggested in the prior art that such wastes can be digested by enzymes and bacteria to produce methane gas and/or by-products. The methane gas can then be utilized to drive a generator set to produce electricity or directly utilized to operate gas fired furnaces or other machinery.

A principal problem in producing energy from organic waste is the difficulty in handling the waste slurry and the cost of maintaining ideal digesting conditions to obtain satisfactory yields of gas. Many prior attempts have required elaborate plumbing and pumping systems as well as the use of mechanical agitators in order to obtain effective digesting of the organic slurries. Often the initial costs are prohibitive and the net energy gain of these complex systems has been too small to justify practical use.

A further problem with proposed systems has been the formation of thick surface scum which effectively blocks the release of gas from the slurry into the collection bubble and adversely affects the generating process itself. Also, the digested solids collect along the bottom of the tank requiring frequent draining and cleaning. These problems further reduce the efficiency of the system and, under certain circumstances, can stop gas generation altogether.

It is accordingly an object of the present invention to provide an improved digester system for organic wastes.

It is a further object of the present invention to provide a digester system including a scum suppression mechanism which will prevent the formation of scum on the surface of the slurry.

A further object of the present invention is to provide a digester system of the type described which dispenses with the need for mechanical agitation to mix the slurry. According to the present invention, stirring of the slurry is attained by use of an improved heat exchanger located in the digester tank.

A further object of the invention is to provide means whereby solids which settle to the bottom of the tank can be periodically removed therefrom without the need for interrupting the operation of the digester or of draining the tank.

BRIEF DESCRIPTION OF THE DRAWINGS

FIG. 1 is a schematic illustration of the digester system according to the invention.

FIG. 2 is a sectional view of the digester tank illustrating the details of the invention.

FIG. 3 is a plan view of the digester tank illustrating the details of the scum suppression system.

FIG. 4 is a cross-sectional view along the lines 4—4 of FIG. 2.

FIG. 5 is a sectional view along the lines 5—5 of FIG. 3.

FIG. 6 is a view similar to FIG. 4 useful in explaining the transverse mixing of the present invention.

FIG. 7 is a view similar to FIG. 2 useful in explaining the sludge handling feature of the invention.

FIG. 8 is a view similar to FIG. 4.

FIG. 9 is a schematic plan view detailing the plumbing arrangement for the sludge handling feature of the invention.

DETAILED DESCRIPTION

Referring now to FIG. 1, an anaerobic digester system according to the invention is illustrated. The system includes a digester 10 having a flexible membrane cover 12 and a fluid receiving tank 14, preferably recessed into the ground. A slurry is fed into the tank through an inlet 16 and removed from the tank via an outlet 18. The inlet is located at one end of the tank while the outlet is at the other end. During operation the slurry passes into the digester tank, remains therein for a predetermined amount of time and is then removed therefrom via the outlet. Depending upon temperature conditions, the type of material contained in the slurry and other process conditions, an ideal residence time in the digester tank can be determined either theoretically or empirically.

The slurry is formed in a sump 20 which is supplied with water from a source not shown and manure or other waste from a conveyor system schematically indicated at 22. The manure is conveyed into the sump 20 for mixing with water to form the slurry. A sump pump 24 conveys the slurry to the inlet 16 of the digester tank.

The digester system according to the present invention produces methane gas which is collected in the flexible cover 12. The gas is removed from the tank through a distributor 30. In the embodiment illustrated, the gas is provided to an internal combustion engine 32 having its carburetor and fuel system appropriately modified to run on the methane gas. The engine 32 is water cooled in the usual manner employing a radiator and fan. In accordance with the present invention, the heat from the engine is provided via a pump 34 to a heat exchanger 36 located in the digester tank 10. As will be described, the heat exchanger 36 warms and stirs the slurry. The stirring is in a direction transverse to the direction of flow of the slurry through the tank as schematically indicated in FIG. 6. Of course, the methane gas can be burned directly in a furnace or other device and the engine 32 omitted. In that case the heat exchanger 36 is supplied with hot water from the furnace or other source such as a water heater.

The output from the internal combustion engine 32, which may be used to drive an electrical generator or to operate machinery, is indicated schematically by the dashed line 38. Provided along the bottom of the digester tank 10 are a plurality of gas jets which are utilized to prevent sludge build up. Provided on the surface of the slurry is a scum suppression assembly 40 which serves to prevent formation of scum which can interfere with the formation and release of methane gas from the slurry.

Referring now to FIG. 2, the system according to the invention can be seen in greater detail. The heat exchanger 36 can be seen to be formed from a continuous length of conduit which doubles back on itself three or more times, as desired, to form a vertical heat exchange element centrally located in the tank and extending from the inlet to the outlet end. As indicated in FIG. 2, the scum suppression assembly 40 can be seen floating on the top of the slurry 42 and includes means which permits adjustment of the scum suppressors to compensate for variations in the level of the slurry. The liquid jets positioned along the bottom of the tank are visible in FIG. 2.

The digester is gas tight and arranged to exclude free oxygen. Thus, the digester is anaerobic and produces methane, carbon dioxide, water and other products in small quantities. The solids introduced in the form of a water slurry preferably constitute approximately 13% of the slurry. While this percentage is not critical, the slurry must be fluid enough to permit ease of transport and escape of gas through the surface. It is estimated that approximately half of the volatile solids in the slurry will be digested by bacteria and converted to biogas and water. Preferably, the average residence time of the slurry is one to three weeks. At the time of the introduction of the slurry into the digester, its temperature is usually less than that desired for proper bacterial action. The newly introduced slurry will therefore sink to the bottom of the tank until warmed by the heat exchanger pipes 36 resulting in a stirring action to be described. Preferably, the temperature range of the digester is maintained between 95° F. and 100° F.

Referring to FIGS. 3 and 5, the scum suppression system according to the invention is illustrated. The water-slurry introduced into an anaerobic digester contains materials which are inclined to float or which, when attached to gas bubbles, may float. Frequently a collection of such materials form a dried scum over the slurry which is detrimental to the digestion process. The scum may form a hard, dry mat which impedes the release of the gas produced by bacterial digestion. In turn, this may reduce or stop the bacterial action.

The suppressor, which contacts the surface of the slurry, prevents the formation of the scum, allowing the digester gases to escape from the slurry. In a digester system in which no mechanical agitation is employed and particularly where "plug flow" is utilized—that is, the entrance of the slurry at one end of the tank and removal at the other end—scum suppression is particularly important.

The scum suppressor system includes a plurality of transversely disposed joists 50 extending partially below the anticipated fluid level in the tank. The joists may be secured at the sides of the tank in an appropriate manner. The joists may be made of treated lumber or, if desired, other materials may be utilized. Disposed longitudinally across the tops of the joists are restraining members 52 spaced at regular intervals. The number and spacing of the restraining members is a function of the size of the suppressor panels 54 which are positioned between the joists 50 and permitted to float on the slurry 42. The restraining members 52 depress the panels 54 into the slurry whenever the slurry level is near the maximum for the tank. This periodic submersion of the scum into the slurry results in eventual digestion of the scum preventing interference with the production and escape of the gas.

The suppressor panels 54 are preferably made of rigid foam. Their dimensions are such that spaces remain between adjacent panels and between the panels and the joists. These spaces permit the escape of the methane gas upwardly into the flexible gas bag 12. The restraining members 52 insure that the foam suppressors 54 do not get mispositioned in the event that the slurry is temporarily higher than the normal operating level.

A nylon rope 56 is secured to the bottom portion of the transverse joists 50 for a similar purpose. The ropes prevent the foam suppressors from dropping out from beneath the joists in the event that the slurry level is temporarily too low as may occur, for example, when the tank is not operating or is being serviced or cleaned. Between the restraining member 52 and the rope 56, the scum suppressor panels 54 are free to move up and down on the surface of the slurry always maintaining contact therewith thereby to inhibit the formation of surface scum.

Referring now to FIGS. 4 and 6, the heat exchange assembly according to the invention will be described. The water-slurry of organic materials introduced into an anaerobic digester can be made to undergo bacterial decomposition if the temperature is suitably maintained. In most cases this requires the introduction of heat to compensate for losses through the walls of the container and to raise the temperature of the incoming slurry. The heat energy must be introduced at a rather low temperature so as to avoid killing the gas producing bacteria and/or caking of the organic slurry. To maximize gas generation, it is desirable to produce a mild stirring of the slurry.

The heat exchanger 36 according to the invention performs both of these tasks. The vertical pipes run the length of the digester container near the bottom thereof. This assembly of pipes passes heat from the hot water flowing inside the pipes to the slurry in the digester. The slurry is fluid enough so that thermal convection currents from the heat exchanger cause the slurry to roll and produce a vertical stirring action. This helps remove the gas and expose the newly introduced slurry to bacterial attack.

FIG. 6 illustrates the resulting stirring action of the heat exchanger 36 when the system is in operation. The hot waste water from the engine 32 passes through the heat exchange pipes 36 heating the slurry along the bottom portion of the tank. This causes the heated slurry to rise resulting in a rotational stirring of the slurry in a direction transverse to the direction of slurry flow. No mechanical agitation of the slurry is required because of this induced agitation from the heat exchange system. The heat exchanger, of course, is also responsible for maintaining the proper temperature for efficient production of gas. For that purpose it is desirable to include in the system a thermostat to monitor the temperature of the tank and the heat exchange pipes and to provide a bypass whereby excess heat from the engine can be disposed of when necessary.

It will be apparent that the heat exchanger 36 could be provided in a form other than illustrated herein and the system would still operate. However, the transverse stirring action would be impaired and it might be necessary to provide mechanical agitation resulting in additional costs and less effective use of the slurry.

Referring to FIGS. 7 through 9, the sludge handling feature of the invention is illustrated. The slurry contains materials which are more dense than water at the time of entry or which are inclined to become more dense during digestion. They tend to settle to the bottom and remain in the digester. This retards the flow of the solids through the digester. These solids lodge in the bottom of the tank for an excessive time and detrimentally reduce the effective volume of the digester.

In order to prevent these problems, a plurality of jets 60 are provided along the bottom of the digester tank. The jets are spaced the length of the tank from the input end to the exit end. Each jet is separately connected to a pipe 44 through which water, digester liquid or gas can be pumped under pressure for the purpose of unsettling the solids which have accumulated on the bottom of the tank. As indicated in FIG. 7, the jets are positioned to project the solids towards the exit end of the tank and by sequentially operating the pairs of jets beginning with the input end the accumulated solids may be moved from the input end to the exit end and in the process picked up by the slurry for removal from the digester tank. A typical accumulation of sludge in the bottom of the tank is indicated by the dashed lines 62. By discharging liquid or gas through the jets nearest the inlet end, sludge is shifted towards the central portion of the tank. Subsequent operation of jets closer to the central portion and ultimately the end portion of the tank are effective for shifting the solids to the exit end of the tank for removal.

Referring again to FIG. 5, the manner in which the flexible membrane 12 is secured to the tank is illustrated. The membrane serves to collect and store the methane gas produced by the digester. The membrane 12 is attached to the upper edge of the digester tank in a manner to form a gas tight seal. The edge of the membrane is compressed by a hold down bar 70 which is, in turn, clamped against the wall by clamping member 72 secured by a bolt 74. The membrane 12 passes between the hold down bar 70 and the notch in the wall 76. If desired, the sealing may occur at a point beneath the normal level of the slurry whereby the gas seal is enhanced by the fluid barrier and thus does not depend upon a precision fit of the surfaces or require a gasket.

While embodiments of the invention have been shown and described in some detail, it will be understood that this description and illustrations are offered merely by way of example, and that the invention is to be limited in scope only by the appended claims.

What is claimed is:

1. An anaerobic digester for producing combustible gas from organic waste comprising:
   (a) a digester tank having an input end adapted to receive a fluid slurry containing said organic waste and an output end from which the slurry is discharged from the tank, said tank including an air tight flexible membrane and an outlet therefrom disposed over said tank into which the gas passes as it evolves from the slurry;
   (b) means for introducing the slurry into said tank at said input end and means for removing the slurry from said output end after passage through said tank;
   (c) means for heating the slurry to a temperature conducive to anaerobic digestion of the organic wastes thereby to generate said gas;
   (d) means for suppressing the formation of scum on the surface of the slurry while resident in said tank, said suppressing means including a plurality of panels floatably positioned on the surface of said slurry, whereby scum is maintained below the surface of the slurry in a wet condition to ensure digestion;
   (e) means for maintaining the panels in position to maintain spacing therebetween and means to prevent dislocation thereof when the slurry is above or below normal levels in said tank.

2. The digester according to claim 1 further including means for removing sludge from the bottom of said digester tank, said removing means including a plurality of nozzles having openings into the bottom of said tank along the length thereof; and means for providing fluid under pressure to selected ones of said nozzle openings whereby sequential operation of said openings is effective for moving sludge from the input end to the output end of said tank.

3. The digester according to claim 2 wherein said openings are arranged along the length of the tank and the fluid providing means includes a plurality of pipes each of which communicates with the nozzle openings thereby to permit said sequential operation.

4. The digester according to claim 1 wherein said introducing means includes:
   (a) a sump;
   (b) a conveyor means for supplying organic waste to said sump;
   (c) means for supplying a fluid to said sump for mixing with said waste to form said slurry;
   (d) means for pumping the slurry from the sump to the input end of said tank.

5. The digester according to claim 1 wherein said heating means includes:
   (a) a length of hollow pipe disposed within said tank having a plurality of connected segments arranged one above the other,
   (b) means for pumping a heated fluid through said pipe to heat and stir the slurry through heat transfer and thermal convection, respectively.

6. The digester according to claim 5 wherein said heating means further includes an internal combustion engine having a liquid cooling system and said means for pumping includes a pump communicating the engine cooling system with the hollow pipe whereby the waste heat from the engine is utilized to heat and stir the slurry.

7. The digester according to claim 6 wherein said digester includes means for supplying the gas to said engine whereby the engine runs on the gas generated in said digester.

8. The digester according to claim 1 wherein said panels are made of rigid foam.

* * * * *